United States Patent
Eckmiller et al.

(10) Patent No.: US 6,493,587 B1
(45) Date of Patent: Dec. 10, 2002

(54) DEVICE FOR THE PROTECTED OPERATION OF NEUROPROSTHESES AND METHOD THEREFOR

(75) Inventors: Rolf Eckmiller, Neuss (DE); Valerij Ortmann, Sankt Augustin (DE); Michael Becker, Bonn (DE); Ralph Hünermann, Cologne (DE)

(73) Assignee: Intelligent Implants GmbH, Bonn (DE)

( * ) Notice: Subject to any disclaimer, the term of this patent is extended or adjusted under 35 U.S.C. 154(b) by 0 days.

(21) Appl. No.: 09/635,016

(22) Filed: Aug. 9, 2000

(30) Foreign Application Priority Data

Dec. 23, 1999 (DE) .......................... 199 62 915

(51) Int. Cl.⁷ ................................ A61N 1/37
(52) U.S. Cl. .......................... 607/31; 623/24
(58) Field of Search ............... 607/60, 31, 32, 607/30, 45, 54, 56, 57; 623/11.11, 24

(56) References Cited

U.S. PATENT DOCUMENTS

| | | |
|---|---|---|
| 4,305,397 A | 12/1981 | Weisbrod et al. |
| 4,361,153 A | 11/1982 | Slocum et al. |
| 4,399,821 A | 8/1983 | Bowers |
| 4,401,120 A * | 8/1983 | Hartlaub et al. ....... 128/419 PT |
| 4,613,937 A * | 9/1986 | Batty, Jr. .................... 364/413 |
| 4,766,516 A | 8/1988 | Ozdemir et al. |
| 4,909,250 A | 3/1990 | Smith |
| 5,365,225 A | 11/1994 | Bachhuber |
| 5,456,692 A * | 10/1995 | Smith, Jr. et al. ............. 607/31 |
| 5,646,456 A | 7/1997 | Udoh et al. |
| 5,696,825 A | 12/1997 | Johnson et al. |
| 5,734,330 A | 3/1998 | Nakamaura |
| 5,855,609 A | 1/1999 | Knapp |
| 5,871,451 A | 2/1999 | Unger et al. |
| 5,891,178 A | 4/1999 | Mann et al. |
| 5,930,362 A | 7/1999 | Daly et al. |
| 5,940,515 A | 8/1999 | Kasavaraju |
| 5,940,799 A | 8/1999 | Bruckert et al. |
| 5,963,621 A | 10/1999 | Dimolitsas et al. |
| 5,987,440 A | 11/1999 | O'Neil et al. |
| 6,002,996 A | 12/1999 | Burks et al. |
| 6,241,704 B1 * | 6/2001 | Peterson et al. ............... 604/65 |

FOREIGN PATENT DOCUMENTS

| | | |
|---|---|---|
| EP | 0896828 A2 | 8/1998 |
| EP | 0946018 A2 | 3/1999 |
| WO | WO 97/00708 | 1/1997 |
| WO | WO 98/10836 | 3/1998 |
| WO | WO 98/29160 | 7/1998 |
| WO | WO 98/36793 | 8/1998 |
| WO | WO 98/36795 | 8/1998 |

* cited by examiner

*Primary Examiner*—Bruce Snow
(74) *Attorney, Agent, or Firm*—Richard C. Woodbridge, Esq; Woodbridge & Associates, PC

(57) ABSTRACT

The invention relates to a system for the protection of neuroprosthesis operation against unauthorized access to the function or operating data. The system is assigned to neuroprostheses for treating functional disorders of the nervous system. This neuroimplant protection system (NIS) comprises at least one neuroprosthesis component which is in contact or operational connection with nerve tissue. Neuroprosthesis operation takes place only during the period of a specific authorization and/or comprises an authorized data transmission between external component and implanted component and/or an authorized communication for monitoring and/or defining the neuroprosthesis functional state. The communication between external and implanted component is in encrypted form.

18 Claims, 5 Drawing Sheets

DEVICE FOR THE PROTECTED OPERATION OF NEUROPROSTHESES AND METHOD THEREFOR

FIELD OF THE INVENTION

The invention relates to a method for the operation of a neuroprosthesis and to a device therefor.

BACKGROUND OF THE INVENTION

In the context of the present patent application, neuroprostheses are understood as meaning devices for use in contact or active connection (unidirectional or bidirectional influencing through release of active ingredients) with the central nervous system inside the skull, the spinal cord (or peripheral nerves connected to the spinal cord) and also optical prostheses or hearing prostheses with an implanted internal component and a non-implanted external component.

Several known neuroprostheses for the treatment of inter alia functional disorders of the vision system, the hearing system, the intracranial nerve system, the vegetative nerve system, the spinal cord or the peripheral nervous system have an implanted component in contact with nerve tissue in which data transmission is provided between an external and the internal implanted component for the purposes of operation, of functional monitoring or of function determination (see for example WO 98/36793, WO 98/36795 and U.S. Pat. No. 6,002,996).

Several systems have been disclosed for protected data transmission between mutually remote components by inter alia mobile radio, satellite communication or in local computer networks or the Internet in for example telebanking, private car theft protection or telesurgery (see for example DE 2618401, U.S. Pat. No. 5,646,456, U.S. Pat. No. 5,734,330, U.S. Pat. No. 5,940,515, U.S. Pat. No. 5,930,362, U.S. Pat. No. 5,963,621, U.S. Pat. No. 5,940,799, DE 19630920 and EP 0946018).

Known implants for inter alia personal identification or animal tracking location are in signal connection with an external component without contact to nerve tissue (see for example U.S. Pat. No. 4,399,821, U.S. Pat. No. 4,909,250, U.S. Pat. No. 5,855,609, WO 97/00708, EP 0896828 A2 and WO 98/29160).

Implants as heart pacemakers whose operating state can be checked and/or altered by means of an external component are known (see for example in U.S. Pat. No. 4,361,153, DE 2944542, U.S. Pat. No. 5,871,451 and U.S. Pat. No. 5,891,178).

There are known encrypting and decrypting devices and methods for avoiding unauthorized access to digital or analogue data transmissions inter alia in industrial or medical-engineering fields of application (see for example U.S. Pat. No. 4,766,516, U.S. Pat. No. 5,365,225, U.S. Pat. No. 5,696,825, U.S. Pat. No. 5,987,440 and WO 98/10836).

Available neuroprostheses or neuroimplants (eg a cochlear implant for deaf people or a retina implant with learning capability for blind people with retina degeneration) do not have an access control that makes access to data and operation dependent on a specific authorization. In principle, the external components specially adjusted for a given implant wearer can be exchanged or mixed up and thus result in appreciable and possibly harmful functional disturbances in the industrial and/or biomedical field.

Furthermore, personal data requiring protection and/or implant data can be retrieved and/or altered without authorization to the detriment of the implant wearer and/or of the implant producer/operator.

A communication connection between the implanted component permanently connected to the implant wearer and an essentially exchangeable external component is typically set up for neuroprosthesis operation without prior attention having been paid to protection against unauthorized data access, etc. Therefore the basic risk of misuse or of an unintenional incorrect operation is significant.

OBJECT OF THE INVENTION

It is therefore an object of the present invention to eliminate these disadvantages and to disclose a neuroimplant protection system (NIS) that prevents unauthorized access.

SUMMARY OF THE INVENTION

Thus viewed from one aspect the present invention provides a method for operating a neuroprosthesis in the central nervous system within the skull, the spinal cord or peripheral nerves connected to the spinal cord, or a vision prosthesis or hearing prosthesis, the neuroprosthesis comprising an implanted internal component and a non-implanted external component, a wireless data transmission being provided between the internal component and the external component, wherein some or all of the data are transmitted only if an authorization signal transmitted by the external component to the internal component has been tested and accepted. Because data transfer or operation of the neuroprosthesis can take place only after authorization with the aid of the implanted component, numerous conceivable types of operational misuse may be prevented.

The preferred embodiments of the authorization procedure are based on essential functional features of the implanted component that cannot be discovered, copied or simulated in the implanted state.

Since the authorization procedure requires the interaction of the implanted component with the external component, data stored in protected form in the internal, the external and (optionally) a further internal component can include not only data for the purpose of the neuroprosthesis but also (for example) economically or legally important personal data.

The construction and authorization system of a neuroprosthesis designed in this way prevents the copying of the individual components.

The neuroimplant protection system (NIS) of the invention provides a neuroprostheses expanded or additionally equipped with a number of important advantages over known neuroprostheses without NIS. This substantially increases the operational security and the acceptance of neuroprostheses in relation to inter alia data protection and protection against operating faults. For the first time, the present invention provides a system that prevents operational misuse by coupling the implanted component to external components not specifically assigned. This ensures for the first time that the implant wearer is protected against functional injury owing to the use of wrong components.

The present invention makes it possible for the first time to prevent unauthorized access to data and function determination of the implanted components for neuroprostheses equipped with NIS.

Furthermore the present invention makes it possible for the first time to prevent unauthorized access to data transmission between external and implanted components. As a result, the personal data protection of the implant wearer (which in the case of conventional treatment methods is protected by inter alia the attendant doctor's duty of confidentiality) is secured permanently for the first time in relation to the neuroprosthesis operation.

In addition, the present invention can prevent the unauthorized access to important functional properties of the neuroprosthesis. This prevents the unauthorized imitation (reverse engineering) of components of the neuroprostheses because (on the one hand) important functional properties are lacking for the unauthorized imitation and (on the other hand) such unauthorized imitation components cannot be operated with the remaining components because of lack of compatibility and lack of authorization of the component communication.

DESCRIPTION OF THE PREFERRED EMBODIMENTS

Exemplary advantageous embodiments of the neuroimplant protection system (NIS) and of the associated methods are discussed below with reference to the drawings.

Figure 1:
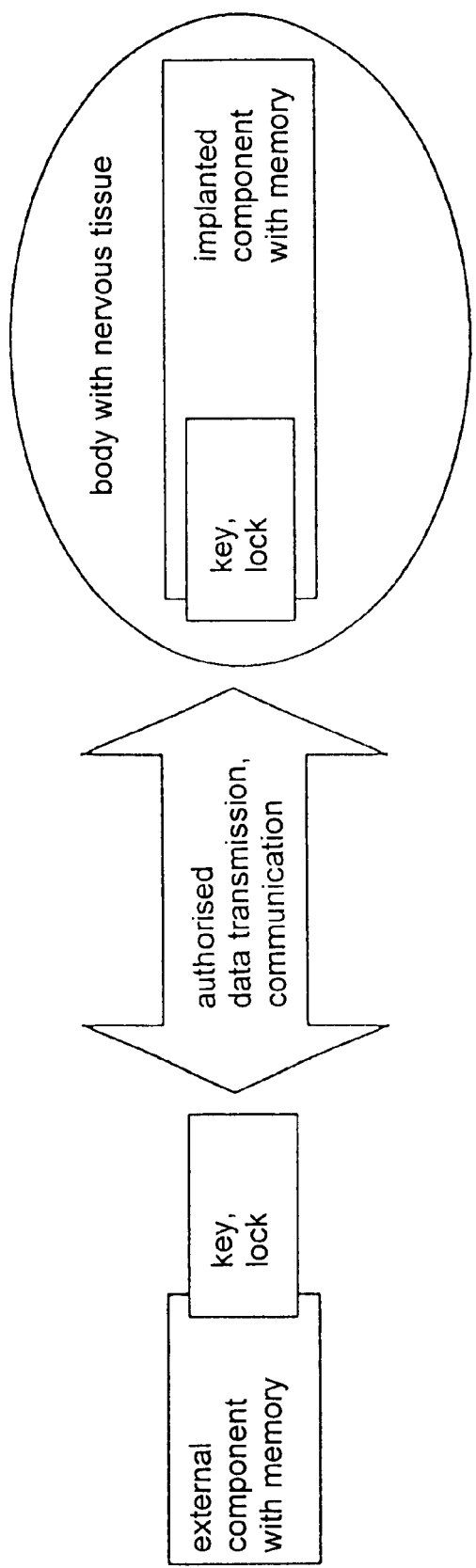
FIG. 1 shows an arrangement of the neuroimplant protection system (NIS) for a neuroprosthesis.

FIG. 1 shows an arrangement of the neuroimplant protection system (NIS) for a neuroprosthesis. Both the external component of the neuroprosthesis and the implanted, internal component have a key and/or a lock for testing and performing authorized data transmission and/or for requesting and/or redefining the functional state of the individual components.

The operation of the neuroprosthesis or the authorized access to internally or externally stored data is only possible if an authorization signal arriving at the internal component from the external component is legitimized by a method which is based solely on features of the internal component and cannot be analysed, altered or circumvented by any external component.

Figure 2:
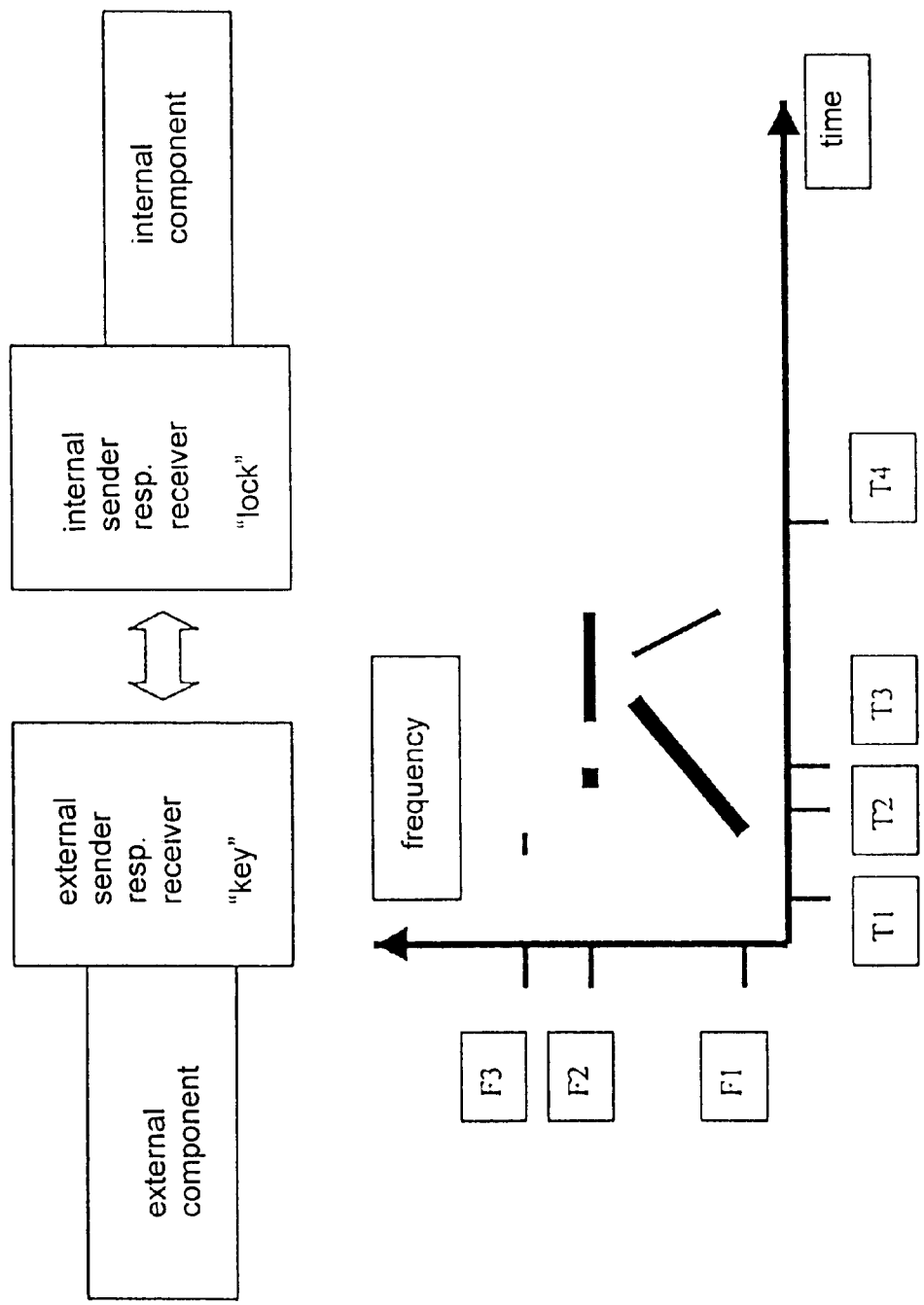
FIG. 2 shows an arrangement of an external component (key) and an internal component (lock) assigned during manufacture.

FIG. 2 shows the arrangement of an external component (key) and internal component (lock) assigned during manufacture without any possibility of the key or the lock being discovered by analysis of the external component. In the illustrated preferred embodiment shown, it is assumed that the frequencies F1, F2, F3 and also the temporal sequence T1, T2, T3, T4 were selected during the manufacture of the lock and key from a greater frequency range (sound, electromagnetic waves, light, noise generator, etc.) for the simple example of the authorization signal shown in the frequency/time diagram. Furthermore the illustrated frequency/time pattern was selected for said key and lock for the purpose of authorization or identification. The associated parameter and function definitions in the external and in the internal component took place during or after manufacture, partly through definitions in the associated microelectronics or micromechanics and partly through definitions in the software.

Figure 3:
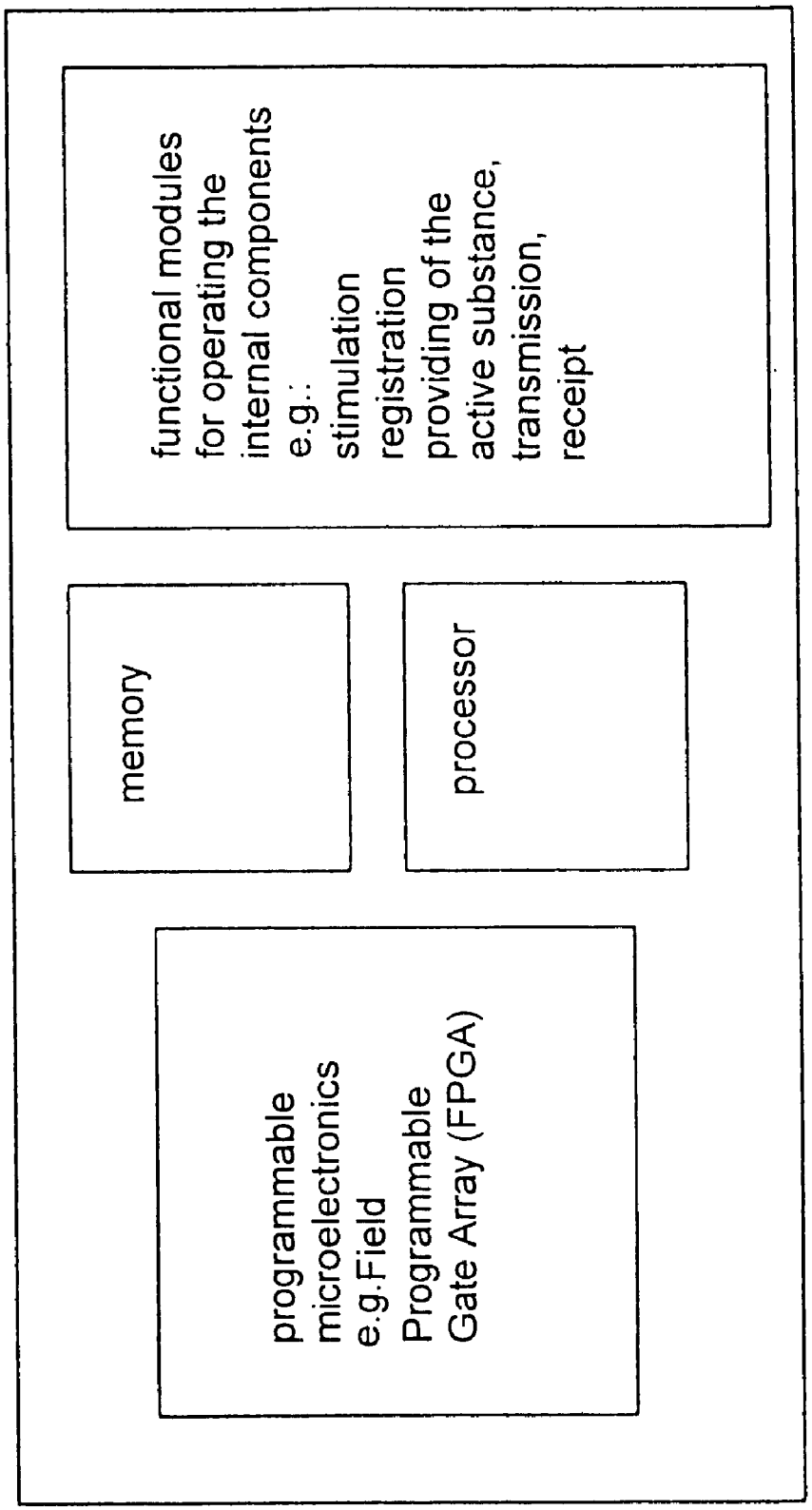
FIG. 3 shows the arrangement of a preferred implementation of the microelectronic determination of the key/lock function in the implanted internal component znd in the external component respectively.

FIG. 3 shows the arrangement of a preferred implementation of the microelectronic definition of the key/lock function in the implanted internal component or in the external component. The selected authorization signal is (for example) a signal pattern which is defined by amplitude, frequency, time and position parameters (comparable in principle to the vocalization of an animal). For the purpose of authorization, a type of labyrinth that represents the lock which can be traversed by a unique authorization signal (the key) is produced (in a preferred embodiment) by the interaction of a memory, a processor and FPGA (or the like) during or after manufacture. In a preferred embodiment, the correct traversal of the labyrinth is in this sense a temporal signal pattern that is conveyed in a microelectronically defined form to a logic gate structure and is interpreted as "yes=authorization can take place". Neither the structure and function of the labyrinth nor the gate function or structure that is coupled along the labyrinth and that is assigned completely to the implanted, internal component can be rendered transparent, copied or simulated by actions on the part of the external component.

Figure 4:
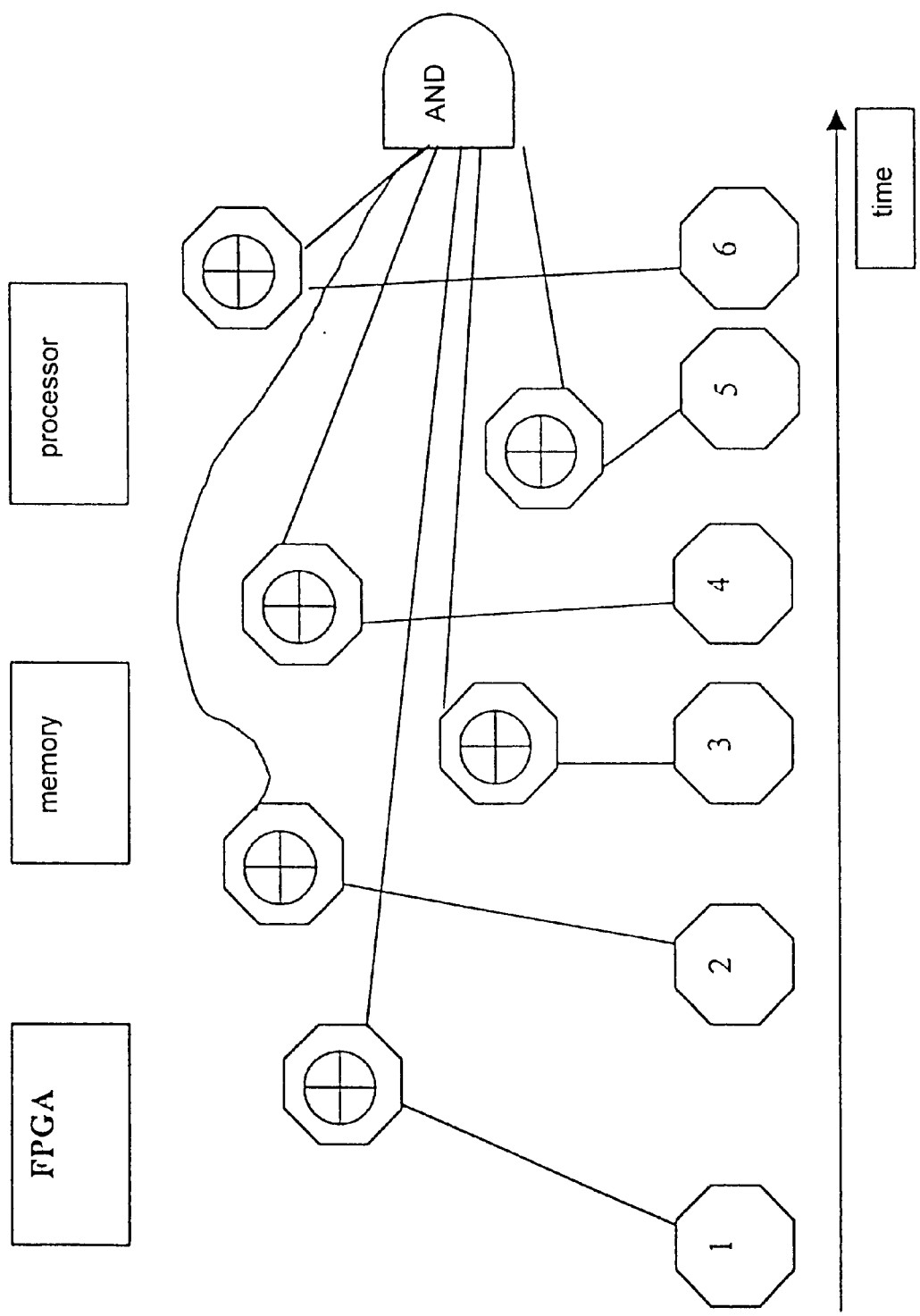
FIG. 4 shows the arrangement of a preferred embodiment of a 'dynamic labyrinth' for representing the second authorization signal as a lock in the internal component.

FIG. 4 shows the arrangement of a preferred embodiment of a 'dynamic labyrinth' for representing the second authorization signal as a lock in the internal component. The 'dynamic labyrinth' (indicated to a small degree at the bottom of FIG. 4 by a sequence of instructions or digital states of which (for example) six can be continuously observed as coupling points 1 to 6) may preferably be represented by an algorithm that is embodied by a defined combination of programmable microelectronics (for example FPGA), memory and/or processor and that assigns the individual elements of an incoming signal to respective logic functions and information processing paths so that the signal is distributed as a function of time over said labyrinth or progresses stepwise. In a preferred embodiment, provision is made that is carried out only if the signal received from the external component as authorization signal (and consequently as a key on the basis of the programmable hardware, memory and processor of the internal component) reaches coupling points 1 to 6 at the prescribed times with the values agreed in each case for the authorization and is detected at them (for example) by a switching network or switching mechanism (logic units indicated as octagons with a cross and a circle including time delay elements with the connecting lines indicated. The output signals of the switching network are evaluated in turn by the AND gate indicated on the right in a narrow time window as a logic 1. The associated time definitions and logic and also labyrinth definitions are not available in this preferred embodiment explicitly as algorithms but are the definitions that are embedded in the internal component and that cannot be discovered and (because of the implantation) are not accessible. Neuroprostheses operation, data transmission and/or access to protected memory areas of the individual components can take place only if authorization has taken place. The authorization can be renewed during operation, in which case (in a preferred embodiment) the authorization signal used for the primary authorization is not used repeatedly but a new signal is used.

Figure 5:
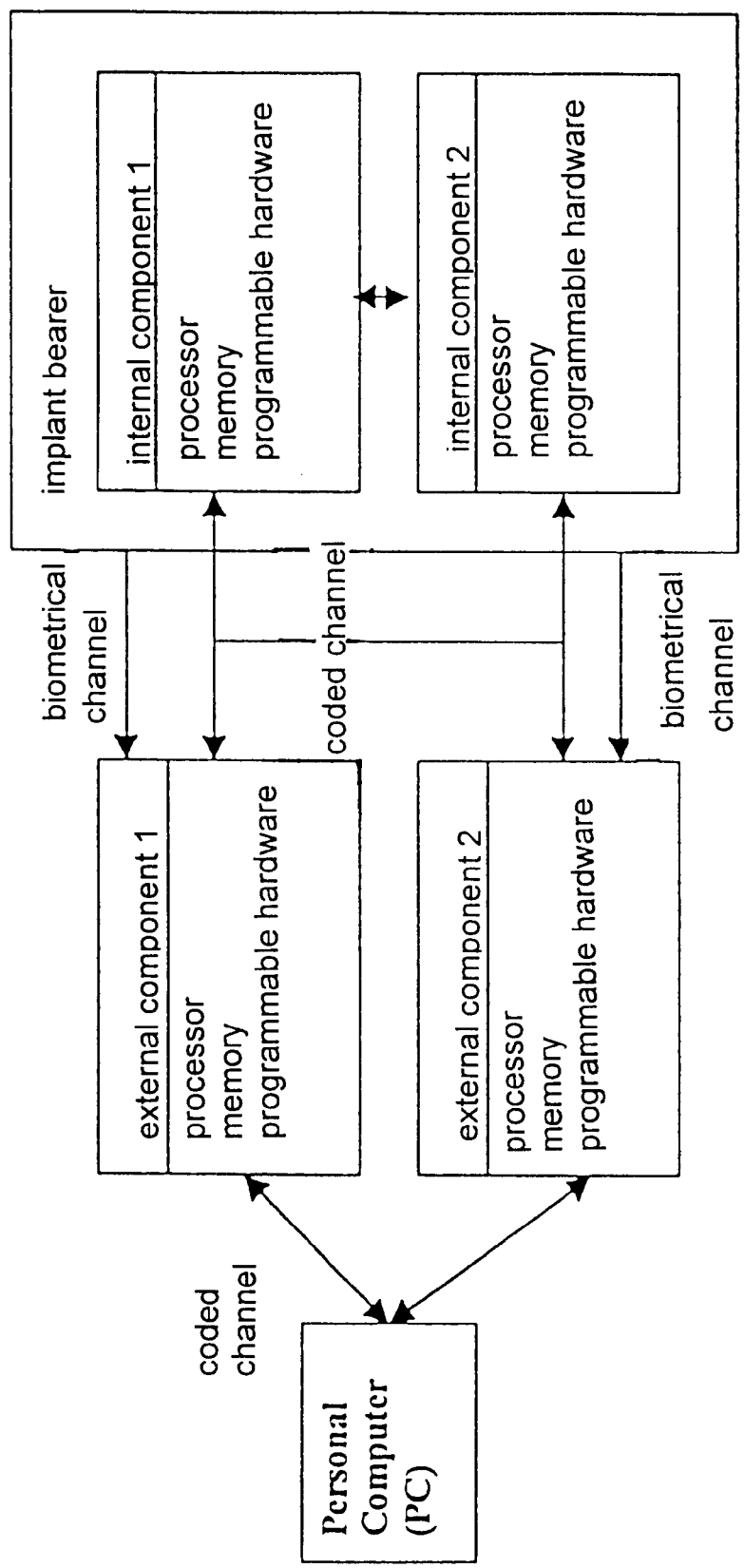
FIG. 5 shows a further preferred embodiment for the arrangement of the neuroimplant protection system (NIS).

FIG. 5 shows a further preferred embodiment for the arrangement of the neuroimplant protection system (NIS). An NIS comprises (for example) two implanted components and protected data transmission channels for communication between a implanted components and also between internal components and (for example) two external components and/or a PC and also (for example) for the transmission of biometric data from the implant wearer to one of the external components and/or a PC. The communication takes place in encrypted form. The external and internal components contain for this purpose necessary encrypting hardware and/or software based on a processor and/or programmable hardware and/or memories. The operation takes place only after a successful authentication and authorization of all the components.

In an advantageous embodiment of the method for the protected operation of a neuroprosthesis (see FIGS. 1, 2, 3, 4, 5), the external component exchanges an encrypted authorization signal by means of an electromagnetic current (for example as a frequency-modulated pulse group) and/or optoelectronic method (for example as an amplitude-modulated pulse group of a laser diode as transmitter to a photosensor as receiver implanted immediately underneath the skin or inside the eye) or on the basis of other physical or chemical principles (such as for example the modulation of sound including body-borne sound with technically known transmitters and receivers) or the specific application of a mechanical signal (for example the generation of vibration patterns by one or more locally distributed, very locally acting vibrators in communication with suitable technically known vibration sensors) with a substructure specially designed and/or positioned for this purpose of the implanted internal component for the purpose of the required authorization for the neuroimplant operation and/or for data transmission between external and internal component.

In a further advantageous method for protected operation embodies, the internal implanted component has (in addition to a periodic timer) a non-periodic timer that divides the time in accordance with a fixed code and requires a copy of this time-code timer in the external component for the purpose of authorization. For this purpose, an algorithm for generating mutually identical, non-periodic temporal sequences is defined during the production or alignment of external and implanted internal components in the two components. Furthermore, in this preferred embodiment, the synchronism of the two non-periodic timers is ensured (for example) by agreed synchronization signals. Consequently unauthorized attempts to gain access to data or operate the neuroprosthesis (which are typically based on periodic timers) can be very rapidly detected and rejected.

In a further advantageous embodiment of the method for protected operation, (depending on definition) in the event of rejection of the authorization attempt, the internal component can either emit a rejection signal or behave passively and thus keep its existence and (optionally) precise localization secret.

In a further advantageous embodiment of the method for protected operation, (depending on definition) the acceptance of an authorization can be variably converted in the neuroprosthesis by: a) automatic start of operation or data transmission without a separate acceptance signal, b) generation of a signal that is transmitted by the internal component and that can also be detected by suitable, externally positioned sensors without access to the corresponding code and c) adjustment of a passive property of the internal component (for example the switching-on of an internal energy receiver, of an oscillatory circuit or of absorption or reflection structures) that is measurable externally (for example through increased energy drain) by the specially authorized component which transmits (for example) in the authorized code so that it cannot be discovered by foreign external detectors.

In a further advantageous embodiment of the method for protected operation, to avoid operational misuse an internal component is always assigned only to precisely one external component and vice versa. This unambiguous exclusive assignment is achieved in such a way that it cannot be disabled by access monitoring mechanisms current in data processing by means of "superuser" rights (for example) of the implant operator or producer or through knowledge of a password. For example, the replacement of a specific external component originally assigned to the internal component can take place only through the express agreement of the implant wearer by way of agreement to a medical intervention. For this advantageous purpose, a functional real-time model of the specific external component can be produced only during authorized operation. Alternatively during manufacture or initial alignment of an external and internal component, a duplicate of the external component can be produced such that is securely safeguarded so that only the implant wearer can have access to the "copy" as a model or duplicate of the module for authorization and data exchange of the external component.

In a further advantageous embodiment of the method for protected operation, the attainment of authorized access to data transmission and/or internal component is not possible outside the authorized operation by a functional analysis of the specific external component or the functional real-time model assigned to it. This advantageous property is achieved inter alia in that the properties detectable in the external component during the analytical operation do not give adequate information about the coding or encrypting necessary for the successful authorization and decoding or decrypting of the authorization signal. For this purpose, the authorization is preferably configured in such a way that a multidimensional "template match" comprising (for example) the dimensions of time, amplitude, frequency and position which was defined in the manufacture of one internal component in each case and the associated external component in a random process or with the aid of neuronal networks or other learning algorithms or using features specific only to the implant wearer (such as (for example) iris of the eye, fingerprint, inherited material) forms a non-interchangeable "key-lock" pair. In this context, in a functional and structural analysis of the external component, neither the external "key" nor the associated internal "lock" can be determined at reasonable expense. The large number of possible combinations is such that the prescribed number of futile authorization attempts is very rapidly reached and the internal component permanently disabled.

In a further advantageous embodiment of the method for protected operation, for the production or the initial alignment or functional definition of an external and an internal component (and optionally a duplicate to be securely safeguarded of the external component in relation to the coding elements), pairs of the associated memories or/and processor and/or FPGA units are in each case processed by identical software and/or hardware definitions. For example, the corresponding pair of programmable microelectronic units (for example, FPGA) can be programmed taking into account its physical and geometrical properties by an identical program or can be produced by mechanical manufacturing steps, as a result of which (for example) the non-periodic timer or the definition of the family of authorization signals used only for said pair is defined unambiguously, confidentially and in a protected manner (namely embedded in the microelectronics). However, owing to the function sequences differently defined in the external and the internal component and additional functions, these identical function definitions do not bring about identical overall functions, but precisely complementary functions unambiguously matching one another. These may be function definitions that can be repeated or not repeated by the producer. As a result, pairs are produced that can communicate or exchange signals only with one another but not with other components.

In a further advantageous embodiment of the method for protected operation, access to protected data or functional states both in the internal component and in the external component is made (or can be made) dependent on the successful authorization. For this purpose, in a preferred embodiment, an authorization attempt legitimized in the internal component is also registered in the external component and used therein not only to unblock the data transmission but also to unblock the access to data or functional states available in protected form in the external component.

In a further advantageous embodiment of the method for protected operation, the selected authorization signal is (for example) a signal pattern that is defined by amplitude, frequency, time and position parameters. Every external component has as an authorization signal its unambiguous identification as authorization key. Every internal component has in turn another authorization signal as authorization lock. Knowledge of the key or of the lock alone does not permit conclusions to be drawn about the other signal needed in each case for authorization. Data transmission and/or neuroprostheses operation can be started only when the correct authorization signal is received as a key in the internal component and is successfully compared with the authorization signal in the latter available as a lock using a memory and/or a processor and/or an FPGA so that the key and lock jointly result in an authorization decision.

For the abovementioned purpose, in a preferred embodiment a type of 'dynamic labyrinth' (FIG. 4) that represents the authorization signal of the internal component and that can be traversed only by one correct authorization signal as key is generated by the possible combination of memory, processor and programmable hardware (see FIG. 3) during or after production.

In a preferred embodiment, the correct traversal of the 'labyrinth' generates in turn a temporal signal pattern that is conveyed in a microelectronically defined form to a logic gate structure and is interpreted as "yes=authorization can take place". Neither the structure and function of the labyrinth nor the gate function or structure that is coupled-on along the labyrinth and that is completely assigned to the implanted internal component can be rendered transparent, copied or simulated by interference on the part of the external component.

In a further advantageous embodiment of the method for protected operation, the 'dynamic labyrinth' is represented preferably by a sequence of instructions or digital states of which some are observed continuously as coupling points (see FIG. 4) or by an algorithm that is implemented by a defined combination of programmable hardware, memory and/or processor. This preferred labyrinth algorithm assigns the individual components of an incoming signal to logic functions and information processing paths in each case so that the signal is distributed as a function of time over said labyrinth or progresses step-wise in it.

In a preferred embodiment, the labyrinth (which can be implemented as an algorithm in accordance with the prior art for example in an FPGA, memory and/or processor) functionally comprises a number of paths with bifurcations, direction definitions and gates that change as a function of time. A typical attempt to traverse the labyrinth successfully comprises the division of the signal into individual signal elements that are started at different points in the labyrinth and whose time variation has to match the time variation of the particular labyrinth path precisely. only if the signal elements change in a way that precisely matches the labyrinth path (for example in relation to speed and direction of movement) can the required test signals occur at the defined coupling points at the required times. In this preferred embodiment, it is the case that the authorization is carried out only if the signal received from the external component reaches (as authorization signal and consequently as a key on the basis of the specifically defined labyrinth traversal) the coupling points at the prescribed times with the value agreed in each case for the authorization and is detected at said points (for example) by a switching network or switching mechanism (preferably comprising logic units or functions including time delay elements and connecting lines to the individual coupling points) and the output signals of the individual switching network elements (see FIG. 4) are evaluated in turn as a logic 1 by the AND gate indicated on the right in a temporally coincident manner or in a narrow time window. In this connection, the coincidence of the results detected at different times at the coupling points is achieved by time delay elements. The associated time definitions and logic definitions of the switching network as a test system for the association of key and lock and also the definitions representing the lock are embedded in the internal component and cannot therefore be discovered and are not accessible due to the implantation.

In a preferred embodiment of the method for protected operation, the completion of the authorization for preventing an unauthorized completion signal at the external component (false signal) is not explicitly signalled to the external component but is achieved only implicitly by the operational start-up of the internal component detectable by the external component. As an alternative to this, the completion can be signalled in each case by a signal from the internal to the external component, which signal can be used only once and (although capable of correct interpretation in the external component) is not explicitly stored.

In a further advantageous embodiment of the method for protected operation, the authorization is altered during operation. This is preferably done so that (even during the definition of the authorization key and lock in connection with the manufacture of external and internal components) the change in the key and/or the lock is prepared (for example) after every successful authorization in the external or the internal component and correspondingly takes place automatically.

In a further advantageous embodiment of the method for protected operation, personal and confidential medical data (such as for example the nature and intended operating mechanism of the neuroprosthesis, the quantity, type or time variation of the therapeutic and/or diagnostic measures) stored in an implanted component are protected by a separate access security arrangement.

In a further advantageous embodiment of the method for protected operation, in the event of an operating fault or other type of emergency, the internal components can be switched off or functionally shut down or switched over to a prepared emergency program using a separate technical method and/or microelectronic device. This method for accessing subfunctions of the internal component preferably uses a magnetostatic principle (that is to say for example the movement of a lever belonging to the internal component with a ferromagnetic component), an inductive principle (that is to say inductive intervention in the internal component), a sound engineering principle (that is to say the interference with a switching mechanism in the internal component by sound signals), a mechanical principle (that is to say for example the excitation of mechanical pressure, suction, movement or vibration detectors in the internal component) or the application of other known physical or chemical principles in order to reach corresponding detectors in the internal component.

In a further advantageous embodiment of the method for protected operation, an inhibit that has previously occurred (see above) is cancelled with the aid of an authentication for which a further key is implemented in the software and/or the hardware of the component during the production of the component (or with the aid of a method mentioned in a previous paragraph).

In a further advantageous embodiment of the method for protected operation, the encrypting of the data exchanged between an external and an internal component (including the authorization signal) changes at not necessarily periodic intervals. Provision is preferably made that the data encrypting and associated decrypting is fixed before the start of the authorization. Furthermore, provision is preferably made that the data encrypting after authorization has taken place changes as a function of the authorization signal last used in a manner defined during manufacture of the lock and key.

The data transmission is encrypted in this advantageous embodiment with the aid of an algorithm for the encrypting and decrypting of data on the basis of public and private keys. Every external and every implanted component of the neuroprosthesis operates a set of keys comprising a private key that is known only inside the respective component and a public key that is additionally known inside the other components. During the production of the components, they are each equipped with a public and a private initial key and also with the public initial keys of the other components. Each component automatically replaces its own set of keys at random time intervals in the order of magnitude of a few seconds. Each component passes the public key to the other components in encrypted form as soon as it has been changed. For the purpose of encrypting the data, each component has electronic conductors, a memory and a processor that jointly represent the implementation of the encrypting algorithm. The data are encrypted in such a way that the encrypting algorithm generates new data from the data, the private key of the transmitting component and from the public key of the component to which the data are to be transmitted. Said data are transmitted and decrypted by the receiving component by means of the public key of the transmitting component and of the private key of the receiving component. The decrypting algorithm is designed so that received data that have been encrypted with keys other than those provided above are ignored by the receiving component.

In a further advantageous embodiment of the method for protected operation, the encrypted communication is constructed on the principle of an encrypting system having a public and a private key. The transmitter of a message (internal or external component) encrypts the message with the private key that is known only in the transmitting component and that is set microelectronically and/or by software during the production of the component. The receiver of said message decrypts it on the basis of the information of the component from which it was sent and with the public key of the transmitting component that was set microelectronically and/or by software during the production of the components. No technical device for reading out the set key is implemented either in the external or in the internal component.

In a further advantageous embodiment of the method for protected operation, an authentication is used to unblock the internal and the external components. In this connection, the software and/or hardware of the components is decrypted or initialized with the aid of unblocking keys. The unblocking is possible only if all the components predefined during the production of the components are present and are communicating with one another. No technical device for the unencrypted reading-out of the set unblocking key is implemented either in the external or in the internal component.

In a further advantageous embodiment of the method for protected operation, in order to avoid copying of the software, the software components of the external and/or internal components are stored in encrypted form during the production. To operate an internal and/or external component, a decryption program is first started that obtains the unblocking key from all the other internal and/or external components through the encrypted channel and decrypts the main program of the component. If at least one key is incorrectly received, the main program is incorrectly decrypted and thereby becomes functionally unusable.

In a further advantageous embodiment of the method for protected operation, the authentication proceeds in a predetermined sequence (for example the unblocking keys from internal components are first read out via the encrypted channel and the software of the external components is decrypted therewith and their hardware component initialized). Alternatively, this takes place on the basis of a stochastic principle.

In a further advantageous embodiment of the method for protected operation, the unblocking key is prepared on the basis of biometric features (for example iris, fingerprint, voice, genetic imprint, brainwaves, bioelectric properties of the tissues) of the implant wearer. This prevents unauthorized operation of the neuroprosthesis in the absence of the implant wearer.

In a further advantageous embodiment of the method for protected operation, an authorization of every component takes place permanently or repeatedly during operation after the authentication and serves to detect possible attacks. The authorization takes place by means of an authorization key. Every internal and external component comprises its own authorization key that is prepared either stochastically and/or on the basis of producer data and/or biometric data of the implant wearer and is set microelectronically and/or by software during the production of the component.

In a further advantageous embodiment of the method for protected operation, a distinction is made between two types of NIS operation: regulated operation and autonomous operation. During regulated operation, communication takes place between the implant wearer and a PC or between the doctor and a PC or between another legitimized person and the PC. Every individual is assigned a unique password that (together with the authorization keys of the internal and/or external components) defines the entitlement to operate the neuroprosthesis. The passwords are subject to the duty of confidentiality.

In a further advantageous embodiment of the method for protected operation, the regulated operation of the neuroprosthesis takes place only after the implant wearer has been put into a psychic and/or physiological state that is unusual for the autonomous operation of the neuroprosthesis and that can be identified with existing electromagnetic or electrochemical or optical or thermal or mechanical sensors. For example, the sleeping state can be identified by means of detecting alpha and beta brainwaves, an increased pH can be measured with a pH sensor, an increased or reduced body temperature (for example) by means of temperature measurement and increased blood circulation in the skin (for example) by means of optical sensors.

In a further advantageous embodiment of the method for protected operation, an authorization takes place according to a state pattern in autonomous operation. The state pattern is defined by authorization keys and/or internal signals and/or states of the internal and/or external components (for example in the case of a neuroprosthesis, the stimulation signals and/or states of the spatial and/or temporal filters are used to describe the state pattern). The internal signals and states unambiguously identify the implant wearer and do not occur in any other neuroprosthesis in the combination of the state pattern.

In a further advantageous embodiment of the method for protected operation, the internal component and/or the external component triggers separate signals both in the case of undesirable functions (such as an incorrect function of the neuroprosthesis, an attempted operational misuse and/or an attempt to access data or a function of the neuroprosthesis (such an attempt not being envisaged for the authorized operation)) and in the case of particular authorized functions (such as for example the scanning of personal data in an internal component). In a preferred embodiment, this alarm signal in the one case or status symbol in the other case is brought to the attention of the implant wearer alone (for example by a triggering sensation that can be detected by means of mechanoreceptors).

We claim:

1. A method for operating a neuroprosthesis in the central nervous system within the skull, the spinal cord or peripheral nerves connected to the spinal cord, or a vision prosthesis or hearing prosthesis, the neuroprosthesis comprising an implanted internal component and a non-implanted external component, a wireless data transmission being provided between the internal component and the external component, wherein some or all of the data are transmitted only of an authorization signal transmitted by the external component to the internal component has been tested and accepted and the authorization signal[]is automatically changed at non-periodic time intervals.

2. The method according to claim 1 wherein the authorization signal accepted by the internal component is assigned exclusively to one external component or assigned exclusively to two external components.

3. The method according to claim 1 wherein the authorization signal accepted by the internal component is part of a data stream that is transmitted from the external component to the internal component, the data stream being encrypted using sets of public and private keys, the public and private keys being automatically changed at random time intervals.

4. The method according to claim 1 wherein the authorization signal is checked in the internal component by means of a programmable memory.

5. The method according to claim 1 wherein the authorization signal is checked in the internal component by means of a fixed topological semiconductor structure.

6. The method according to 1 wherein for the data transmission or functioning of the internal component, at least two operating states are possible that can be activated by means of different authorization signals.

7. The method according to claim 1 wherein in the event of an operational fault with a second authorization method, a switching-off or an emergency program of the internal component can be carried out.

8. The method according to claim 7 wherein the second method employs a functional principle other than the first method.

9. The method according to claim 1 wherein the internal component exchanges data during operation with a further implanted component.

10. The method according to claim 1 wherein the data is transmitted in encrypted form.

11. The method according to claim 10 wherein the internal component contains a programmable key or a key that can be defined by means of a fixed topological semiconductor structure.

12. The method according to claim 1 wherein after a number of tested and unaccepted authorization attempts, the acceptance of further authorization attempts is temporarily or permanently blocked and in that the blocking can be cancelled only by means of an authorization signal not necessary in normal operation.

13. The method according to claim 1 wherein after an accepted authorization, no status signal indicating the authorization is transmitted from the internal component to the external component.

14. A method for operating a neuroprosthesis in the central nervous system inside the skull, the spinal cord or peripheral nerves connected to the spinal cord, or a vision prosthesis or hearing prosthesis, the neuroprosthesis comprising an implanted internal component and a non-implanted external component, the internal component furthermore being in contact or operative connection with the nerve tissue and being able to monitor, influence or replace a function of the nerve tissue during operation, wherein the internal component is operated only if an authorization signal transmitted by the external component to the internal component has been tested and accepted and the authorization signal is automatically changed at non-periodic time intervals.

15. The method according to clam 14 wherein the authorization signal accepted by the internal component is part of a data stream that is transmitted from the external component to the internal component, the data stream being encrypted using sets of public and private keys, the public and private keys being automatically changed at random time intervals.

16. The method according to claim 14 wherein the authorization signal is checked in the internal component by means of a programmable memory and wherein the authorization signal is configured using features specific to an implant wearer.

17. A method for operating a neuroprosthesis in the central nervous system inside the skull, the spinal cord or peripheral nerves connected to the spinal cord, or a vision prosthesis or hearing prosthesis, the neuroprosthesis comprising an implanted internal component and a non-implanted external component, the internal component furthermore being in contact or operative connection with the nerve tissue and being able to monitor, influence or replace a function of the nerve tissue during operation, wherein the internal component is operated only if an authorization signal transmitted by the external component to the internal component has been tested and accepted and wherein the acceptance of the authorization signal is dependent on the internal component detecting an unusual state of an implant wearer.

18. The method according to claim 17 wherein the unusual state is selected from the group consisting of sleeping and altered brainwaves and altered pH and altered temperature and altered blood circulation.

* * * * *